(12) United States Patent
Yi (10) Patent No.: US 11,679,382 B2
(45) Date of Patent: Jun. 20, 2023

(54) NUCLEIC ACID EXTRACTION SYSTEM (71) Applicant: WUHAN EDEBIO TECHNOLOGY LLC., Hubei (CN)

(72) Inventor: Chuli Yi, Wuhan (CN)

(73) Assignee: WUHAN EDEBIO TECHNOLOGY LLC., Hubei (CN)

( * ) Notice: Subject to any disclaimer, the term of this patent is extended or adjusted under 35 U.S.C. 154(b) by 398 days.

(21) Appl. No.: 16/971,665

(22) PCT Filed: Mar. 8, 2019

(86) PCT No.: PCT/CN2019/077403
§ 371 (c)(1),
(2) Date: Aug. 20, 2020

(87) PCT Pub. No.: WO2019/174524
PCT Pub. Date: Sep. 19, 2019

(65) Prior Publication Data
US 2020/0391198 A1    Dec. 17, 2020

(30) Foreign Application Priority Data

Mar. 13, 2018  (CN) .......................... 201810206072.X (51) Int. Cl.
*G01N 35/10* (2006.01)
*B01L 3/02* (2006.01)
(Continued)

(52) U.S. Cl.
CPC ............ *B01L 3/021* (2013.01); *B01F 27/806* (2022.01); *B01L 3/52* (2013.01); *B01L 3/565* (2013.01);
(Continued)

(58) Field of Classification Search
None
See application file for complete search history.

(56) References Cited

U.S. PATENT DOCUMENTS 10,646,869 B2    5/2020  Shirai et al.
11,204,358 B2   12/2021  Tajima
(Continued)

FOREIGN PATENT DOCUMENTS

CN      1597916 A    3/2005
CN      1871348 A   11/2006
(Continued)

OTHER PUBLICATIONS

China National Intellectual Property Office, First Office Action, CN Patent Application No. 201810206072.X, dated Apr. 24, 2020, 19 pages.
(Continued)

*Primary Examiner* — Paul S Hyun
(74) *Attorney, Agent, or Firm* — Fenwick & West LLP (57) ABSTRACT

A nucleic acid extraction system, comprising: a nucleic acid extraction plate, and a pipetting device and positive pressure device that are arranged side by side, the pipetting device comprising: an infusion device, an infusion device mounting frame, an infusion device driving unit, and a plurality of infusion units, each of the infusion units comprising: a reagent supply device and a reagent flow controller; the positive pressure device comprises: a plug, an air pipe, a positive pressure provider and a positive pressure driving device. The nucleic acid extraction system is highly efficiency and low-cost when extracting nucleic acid.

11 Claims, 7 Drawing Sheets

(51) Int. Cl.
  *B01L 3/00* (2006.01)
  *B01L 9/00* (2006.01)
  *C12N 15/10* (2006.01)
  *B01F 27/806* (2022.01)

(52) U.S. Cl.
  CPC .............. *B01L 3/567* (2013.01); *B01L 9/523* (2013.01); *C12N 15/1017* (2013.01); *G01N 35/1002* (2013.01); *B01L 2200/16* (2013.01); *B01L 2300/042* (2013.01); *B01L 2300/0618* (2013.01); *B01L 2300/14* (2013.01); *B01L 2400/0487* (2013.01); *B01L 2400/082* (2013.01); *G01N 35/1009* (2013.01); *G01N 35/1011* (2013.01); *G01N 35/1074* (2013.01)

(56) References Cited

U.S. PATENT DOCUMENTS

| | | | |
|---|---|---|---|
| 2005/0045538 | A1 | 3/2005 | Seto et al. |
| 2005/0161377 | A1 | 7/2005 | Fujimoto et al. |
| 2008/0124249 | A1 | 5/2008 | Mori |
| 2013/0105393 | A1 | 5/2013 | Hiesinger et al. |
| 2013/0115607 | A1 | 5/2013 | Nielsen et al. |
| 2014/0087370 | A1* | 3/2014 | Maeshima ......... G01N 35/0099 435/286.2 |
| 2018/0149669 | A1* | 5/2018 | Voss ....................... B65G 47/82 |
| 2018/0304262 | A1 | 10/2018 | Shirai et al. |
| 2020/0209268 | A1 | 7/2020 | Tajima |

FOREIGN PATENT DOCUMENTS

| | | |
|---|---|---|
| CN | 101103105 A | 1/2008 |
| CN | 201201943 Y | 3/2009 |
| CN | 103038624 A | 4/2013 |
| CN | 103305412 A | 9/2013 |
| CN | 203373347 U | 1/2014 |
| CN | 104136596 A | 11/2014 |
| CN | 104804998 A | 7/2015 |
| CN | 106086003 A | 11/2016 |
| CN | 106167758 A | 11/2016 |
| CN | 106367311 A | 2/2017 |
| CN | 206232713 U | 6/2017 |
| CN | 208574655 U | 3/2019 |
| EP | 2011872 A1 | 1/2009 |
| JP | 2014-020779 A | 2/2014 |
| JP | 2015-139398 A | 8/2015 |
| WO | WO 2008/121121 A2 | 10/2008 |
| WO | WO 2016/125251 A1 | 8/2016 |
| WO | WO 2017/204274 A1 | 11/2017 |

OTHER PUBLICATIONS

PCT International Search Report, PCT/CN2019/077403, dated Mar. 30, 2019, pp. 1-10.

European Patent Office, Extended European Search Report and Opinion, EP Patent Application No. 19767872.5, dated Dec. 6, 2021, 12 pages.

* cited by examiner

NUCLEIC ACID EXTRACTION SYSTEM

CROSS-REFERENCE TO RELATED APPLICATIONS

The present application is the National Stage of International Application No. PCT/CN2019/077403, titled "NUCLEIC ACID EXTRACTION SYSTEM", filed Mar. 8, 2019, which claims priority to Chinese Patent Application No. 201810206072.X, titled "NUCLEIC ACID EXTRACTION SYSTEM", filed with the China National Intellectual Property Administration on Mar. 13, 2018, each of which is herein incorporated by reference in its entirety.

FIELD

The present application relates to the technical field of experimental apparatus, and in particular to a nucleic acid extraction system.

BACKGROUND

When nucleic acids are extracted or purified by magnetic bead method or column method, at least one of an automatic pipetting workstation, a centrifuge or a negative pressure machine is required. The existing process of extracting or purifying nucleic acids includes cell lysis, nucleic acid adsorption, nucleic acid rinse and nucleic acid elution. In this process, by the automatic pipetting workstation and pipette tips, 5 to 6 kinds of chemical reagents for extracting or purifying nucleic acids are transferred to a centrifuge tube to lyse cells, or to an adsorption column to rinse and elute nucleic acids, and the centrifuge tube and the adsorption column are transferred into the centrifuge by the automatic pipetting workstation. Solid-phase impurities in the centrifuge tube are precipitated by centrifugation, and the centrifuge or the negative pressure machine allows the liquid in the adsorption column to overcome the resistance of the membrane and flow down to rinse and elute the nucleic acids on the membrane.

In the process of implementing the present application, the inventor found that the prior art has at least the following problems.

During the conventional extraction or purification of nucleic acids, the automatic pipetting workstation is used for pipetting, which is slow, time-consuming, and costly. For example, the process of transferring one kind of solution at a time is as follows. The pipette tips are lifted after being accurately aligned, then are moved to a reagent basin to draw liquid therefrom, then are moved to the centrifuge tube or the adsorption column or upper mouths of holes on a 96-hole plate to release the reagent and constantly draw and release the liquid to mix the liquid well, and then are moved a dustbin and get discarded. More time is needed if 6 kinds of reagents for extracting or purifying nucleic acids need to be transferred. In addition, when pipetting, not only lots of pipette tips are required, but also the quality requirements of the pipette tips are high. Otherwise, the tips cannot be accurately inserted to extract and draw the liquid. In this way, the cost of pipetting is increased. Generally, during high-flux nucleic acid extraction and purification, at least 6 kinds of solution need to be transferred into one 96-hole plate, which needs 6 boxes of high-quality tips, that is 576 in all. So pipetting in this method when extracting or purifying nucleic acids is inefficient and costly. Besides, when using the centrifuge, the centrifuge tube and the adsorption column need to be repeatedly put into the centrifuge for centrifugation and taken out after centrifugation. Such repeated operations are tedious and time-consuming. In order to reduce the use of centrifuge, a negative pressure machine may be used. Specifically, the adsorption column is inserted into a negative pressure box connected with the negative pressure machine, and the rinse liquid in the adsorption column flows into a waste liquid basin in the negative pressure box due to the negative pressure. However, when using the negative pressure machine, due to the obstruction of the waste liquid basin, the suction of the negative pressure machine is reduced, so that the negative pressure provided by the negative pressure machine is not strong enough. Moreover, the negative pressure generated by the negative pressure machine used in the experiment is not strong at present, so the negative pressure machine can only be used in the rinsing step during nucleic acid extraction, but not in the whole process, which makes the method of extracting or purifying nucleic acids tedious, time-consuming and inefficient.

SUMMARY

In order to solve the problems of low working efficiency and high cost when extracting nucleic acids with the cooperation of the automatic pipetting workstation and the centrifuge or the negative pressure machine in the conventional technology, a nucleic acid extraction system is provided according to an embodiment of the present application. The technical solution is as follows.

A nucleic acid extraction system is provided according to an embodiment of the present application, which includes a mounting frame, a nucleic acid extraction plate, a pipetting device and a positive pressure device, wherein the pipetting device and the positive pressure device are arranged side by side.

The pipetting device includes an infusion set, an infusion set mounting frame, an infusion set drive unit and multiple infusion units. The infusion set includes sealed chambers which correspond to the multiple infusion units in one-to-one correspondence, the sealed chambers are arranged side by side, a needle is provided on the bottom of each sealed chamber, and each needle is in communication with the corresponding sealed chamber. The infusion set is arranged on the bottom of the infusion set mounting frame, the infusion set drive unit is fixed on the installation frame, and the infusion set drive unit is configured to drive the infusion set to move up and down through the infusion set mounting frame.

Each infusion unit includes a reagent supplier and a reagent flow controller. For any infusion unit, a liquid outlet of the reagent supplier is in communication with a liquid inlet of the reagent flow controller, and a liquid outlet of the reagent flow controller is in communication with the corresponding sealed chamber.

The positive pressure device includes a plug, an air pipe, a positive pressure provider and a positive pressure drive device. The plug is provided with an air pipe communicating hole. One end of the air pipe hermetically communicates with the air pipe communicating hole, and the other end of the air pipe hermetically communicates with an air outlet of the positive pressure provider. The positive pressure drive device is fixed on the installation frame and is configured to drive the positive pressure provider to move up and down.

Multiple nucleic acid extraction columns are provided on the nucleic acid extraction plate, and the multiple nucleic acid extraction columns are correspondingly arranged below the needles or the plugs. A liquid inlet of each nucleic acid extraction column is provided with a sealing gasket which is in a sealing fit with the corresponding plug, and the nucleic acid extraction column is detachably and hermetically connected with the corresponding plug.

Specifically, the nucleic acid extraction system further includes a stirring plate, a stirring plate mounting frame and a stirring plate drive device. The stirring plate mounting frame is fixed on the installation frame, the stirring plate drive device is arranged on the stirring plate mounting frame, and the stirring plate is arranged on the bottom of the stirring plate mounting frame. Stirring rods in one-to-one correspondence with the multiple nucleic acid extraction columns are provided on the bottom of the stirring plate, and the stirring plate drive device is configured to drive the stirring rods to move up and down in the nucleic acid extraction columns through the stirring plate mounting frame.

Moreover, the nucleic acid extraction system further includes a first partition plate and a first partition plate drive device. The first partition plate is arranged between the stirring rods and the nucleic acid extraction plate. The first partition plate drive device is fixed on the installation frame and is configured to drive the first partition plate to move horizontally below the stirring rods.

Moreover, each of the nucleic acid extraction columns includes a filter column. The filter column includes a breakable member and multiple filter members. The breakable member is arranged between the liquid inlet of the nucleic acid extraction column and the liquid outlet of the nucleic acid extraction column, and is fixed on the nucleic acid extraction column. The breakable member is provided with a groove, and the bottom of the stirring rod is of a conical structure for piercing the groove. The stirring rod is sleeved with a stirring sheet, and an outer diameter of the stirring sheet is less than an inner diameter of the nucleic acid extraction column. The multiple filter members are arranged between the breakable member and the liquid outlet of the nucleic acid extraction column, and are respectively fixed on an inner wall of the nucleic acid extraction column. Each filter member is provided with multiple filter micropores, and in two adjacent filter members, a pore diameter of the filter micropore of one filter member close to the liquid inlet of the filter column is greater than the pore diameter of the filter micropore of another filter member close to the liquid outlet of the filter column.

Moreover, each of the nucleic acid extraction columns includes an absorption column. The absorption column includes a breakable member and an absorption membrane. The absorption membrane covers the liquid outlet of the nucleic acid extraction column. The breakable member is arranged between the liquid inlet of the nucleic acid extraction column and the absorption membrane, and is fixed on the inner wall of the nucleic acid extraction column. The breakable member is provided with a groove, and the bottom of the stirring rod is of a conical structure for piercing the groove. The stirring rod is sleeved with a stirring sheet, and an outer diameter of the stirring sheet is less than the inner diameter of the nucleic acid extraction column.

Moreover, the nucleic acid extraction system further includes a first slide rail. The stirring plate, the pipetting device and the positive pressure device are arranged side by side. The first slide rail is arranged on the installation frame along an arrangement direction of the stirring plate, the pipetting device and the positive pressure device. The first slide rail is correspondingly arranged below the stirring rods, the infusion set and the plugs, and the nucleic acid extraction plate is slidably arranged on the first slide rail.

Moreover, the nucleic acid extraction system further includes a nucleic acid collection plate, a lifting device, a position-limiting snapping frame and a position-limiting snapping frame drive device. The position-limiting snapping frame is slidably arranged on the first slide rail, and the lifting device is arranged below the first slide rail. The lifting device includes a lifting motor, a lifting device screw rod, a lifting device screw nut, a lifting position-limiting plate, a lifting plate and a second slide rail for slidably supporting the nucleic acid collection plate. The lifting motor is fixed on the installation frame, the lifting device screw rod is in transmission connection with an output shaft of the lifting motor, the lifting device screw nut is sleeved on the lifting device screw rod, the lifting position-limiting plate is provided with a lifting snapping groove, and the lifting plate is snapped in the lifting snapping groove. The lifting device screw nut passes through the lifting position-limiting plate to be fixedly connected with a bottom surface of the lifting plate, the nucleic acid collection plate is arranged on a top surface of the lifting plate, and the second slide rail is flush with a top surface of the lifting position-limiting plate and is in parallel with the first slide rail.

The position-limiting snapping frame drive device includes a belt, belt pulleys, a fixing rod and a motor fixed on the installation frame. The fixing rod is fixed on a side wall of the first slide rail. Two belt pulleys are provided and are respectively installed on the output shaft of the motor and the fixing rod. The belt is sleeved on the two belt pulleys, and is in parallel with the first slide rail. The position-limiting snapping frame is fixed on the belt, a first snapping groove for snapping the nucleic acid extraction plate is provided on the top surface of the position-limiting snapping frame, and the nucleic acid extraction plate is arranged in the first snapping groove. A second snapping groove for snapping the nucleic acid collection plate is provided on the bottom surface of the position-limiting snapping frame. Before the nucleic acids are eluted, the nucleic acid collection plate is snapped in the second snapping groove through the lifting device, and the nucleic acid collection plate is provided with nucleic acid collection tubes which are in one-to-one correspondence with the nucleic acid extraction columns.

Specifically, the nucleic acid extraction system further includes a gripping frame for gripping the nucleic acid extraction plate and a gripping drive device. A claw corresponding to one edge of the nucleic acid extraction plate is rotatably provided on the bottom of the gripping frame. A reset spring for resetting the claw is provided between the claw and the gripping frame. The gripping drive device is fixed on the installation frame and is configured to drive the gripping frame to move up and down.

Moreover, the nucleic acid extraction system further includes a second partition plate and a second partition plate drive device. The second partition plate is arranged below the claw. The second partition plate drive device is fixed on the installation frame and is configured to drive the second partition plate to move horizontally below the claw.

Specifically, a liquid level detection device is provided on a side wall of the positive pressure provider.

Further, the nucleic acid extraction system further includes a pressure sensor and a pressure alarm. The pressure sensor is arranged on an outer wall of the air pipe and configured to detect the pressure in the air pipe. When the pressure detected by the pressure sensor exceeds a preset pressure range, the pressure alarm issues an alarm.

The beneficial effects brought by the technical solutions provided by the embodiment of the present application are as follows: The nucleic acid extraction system provided by the embodiment of the present application controls the infusion status of each infusion reagent flow controller. When a chemical reagent in a certain reagent supplier needs to be outputted, the chemical reagent can be transported from the reagent supplier into the sealed chamber of the infusion set at fixed time and by fixed quantity through the reagent flow controller, and can be high-pressure outputted through needles, which enables the nucleic acid extraction system provided by the embodiment to dispense with the pipetting workstation and the pipette tips, thus improving the pipetting speed, efficiency and reducing the cost. Besides, since the plug hermetically communicates with the nucleic acid extraction column, a high-pressure gas can be introduced into the nucleic acid extraction column by the positive pressure provider, and the liquid in the nucleic acid extraction column can quickly pass through and flow out, thus further improving the nucleic acid extraction efficiency.

BRIEF DESCRIPTION OF THE DRAWINGS

In order to more clearly illustrate technical solutions of the embodiments of the present application, the drawings used in the description of the embodiments are briefly described below. It is apparent that the drawings in the following description show only some embodiments of the present application, and other drawings may be obtained by those skilled in the art based on the drawings without any creative efforts.

DETAILED DESCRIPTION OF THE EMBODIMENTS

In order to make objects, technical solutions and advantages of the present application clearer, the embodiments of the present application are further described below in conjunction with the accompanying drawings.

Embodiment

Figure 1:
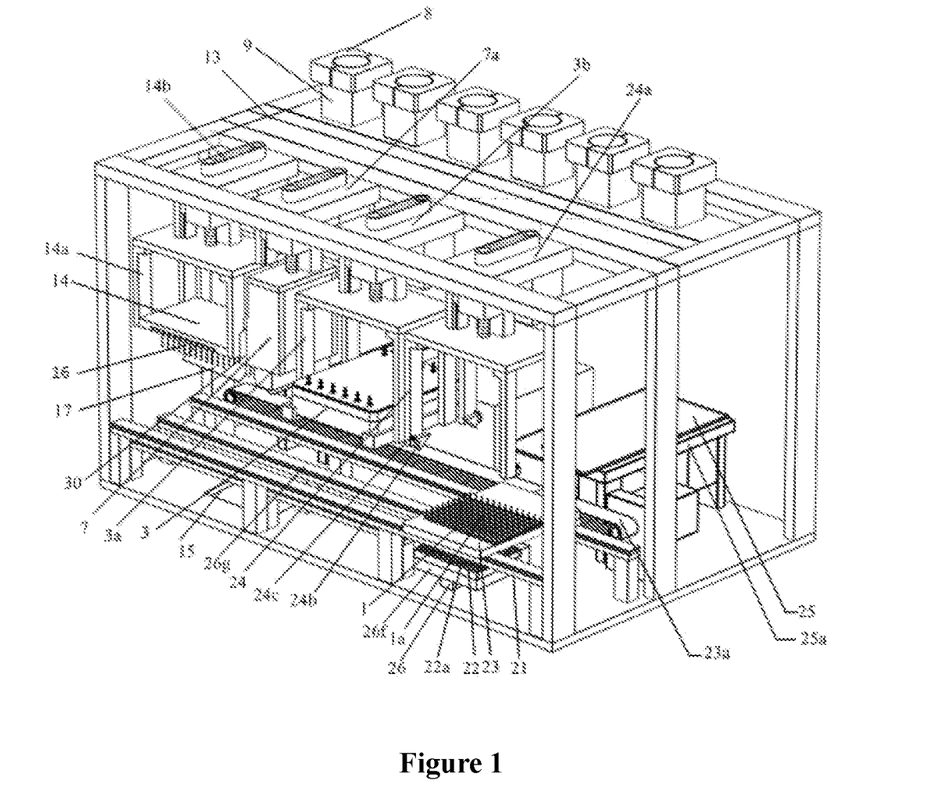
FIG. 1 is a schematic structural view of a nucleic acid extraction system according to an embodiment of the present application.

A nucleic acid extraction system is provided according to an embodiment of the present application, as shown in FIG. 1, which includes a mounting frame 13, a nucleic acid extraction plate 1, a pipetting device and a positive pressure device 7 which are arranged side by side.

The pipetting device includes an infusion set 3, an infusion set mounting frame 3a, an infusion set drive unit 3b and multiple infusion units. Further referring to FIG. 2, the infusion set 3 includes sealed chambers 5 which correspond to the multiple infusion units in one-to-one correspondence, the sealed chambers 5 are arranged side by side, a needle 6 is provided on the bottom of each sealed chamber 5, and each needle 6 is in communication with the corresponding sealed chamber 5. The infusion set 3 is arranged on the bottom of the infusion set mounting frame 3a, the infusion set drive unit 3b is fixed on the installation frame 13, and the infusion set drive unit 3b is configured to drive the infusion set 3 to move up and down through the infusion set mounting frame 3a.

Figure 2:
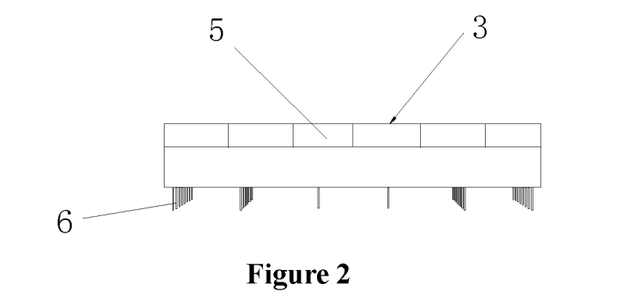
FIG. 2 is a schematic structural view of an infusion set according to an embodiment of the present application.

Each infusion unit includes a reagent supplier 8 and a reagent flow controller 9. For any infusion unit, a liquid outlet of the reagent supplier 8 is in communication with a liquid inlet of the reagent flow controller 9, and a liquid outlet of the reagent flow controller 9 is in communication with the corresponding sealed chamber 5. In the implementation, the liquid outlet of the reagent supplier 8 is in communication with the liquid inlet of the reagent flow controller 9 through a reagent output pipe, and the liquid outlet of the reagent flow controller 9 is in communication with the corresponding sealed chamber 5 also through the reagent output pipe. The reagent output pipe may be a rubber hose. The rubber hose has a certain flexibility, and can adapt to the reagent supplier 8, the reagent flow controller 9 and the sealed chamber 5 in different positions, so that the reagent supplier 8, the reagent flow controller 9 and the sealed chamber 5 can be reasonably arranged to reduce the volume of the nucleic acid extraction system. In the present embodiment, eight needles 6 are arranged at the bottom of each sealed chamber 5, and the eight needles 6 are arranged side by side. A water level alarm (not shown) may be provided in the reagent supplier 8. When the reagent in the reagent supplier 8 is about to run out, the water level alarm can remind the operator to replenish the reagent supplier 8 with the reagent in time.

Figure 3:
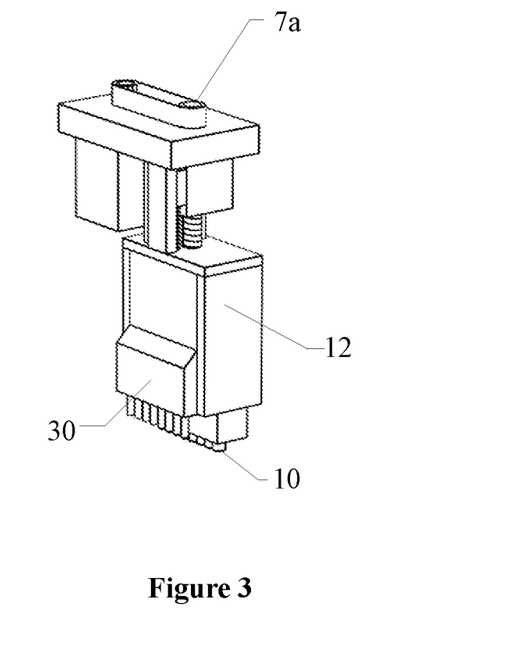
FIG. 3 is a schematic structural view of a positive pressure device according to an embodiment of the present application.

As shown in FIG. 3, the positive pressure device 7 includes a plug 10, a positive pressure provider 12 and a positive pressure drive device 7a. The plug 10 is provided with an air pipe communicating hole. An air outlet of the positive pressure provider 12 hermetically communicates with the plug 10 through an air pipe and the air pipe communicating hole. The positive pressure drive device 7a is fixed on the installation frame 13 and is configured to drive the positive pressure provider 12 to move up and down. The pressure provided by the positive pressure provider 12 may be 100 kPa or more. The positive pressure provider 12 may be an air compression pump, a piston pump, a diaphragm pump or a liquid nitrogen bottle. In the present embodiment, multiple positive pressure devices 7 may be provided, and the multiple positive pressure devices 7 are arranged side by side.

Further, the nucleic acid extraction system further includes a pressure sensor and a siren (not shown), wherein, the pressure sensor is arranged on an outer wall of the air pipe to detect the pressure in the air pipe, and the siren is connected with the pressure sensor. When the pressure detected by the pressure sensor exceeds a preset pressure range, the siren issues an alarm to prompt system check to determine whether the air outlet end is blocked or the air supply end is underpressure. Such that the problems can be solved in time, thereby ensuring the smooth extraction of nucleic acids. Specifically, the above preset pressure range can be obtained according to specific experimental operations, which is not limited here. In addition, how to connect the siren with the pressure sensor to realize that the siren issues an alarm when the pressure detected by the pressure sensor exceeds the preset pressure range is a conventional technology well known to those skilled in the art. In order to save words, it will not be discussed here.

Referring to FIG. 1 again, multiple nucleic acid extraction columns 1a are provided on the nucleic acid extraction plate 1, and the multiple nucleic acid extraction columns 1a are correspondingly arranged below the needles 6 or the plugs 10. A liquid inlet of each nucleic acid extraction column 1a is provided with a sealing gasket 11 which is in a sealing fit with the corresponding plug 10, and the nucleic acid extraction column 1a is detachably and hermetically connected with the corresponding plug 10. In the present embodiment, ninety six nucleic acid extraction columns 1a are provided, a 96-hole plate may be used in the implementation, and multiple plugs 10 may be provided. Each plug 10 is in communication with the air outlet of the positive pressure provider 12 through the air pipe communicating hole. The multiple plugs 10 may be arranged in one-to-one correspondence with the multiple nucleic acid extraction columns 1a.

A disposable anti-contamination plate (not shown) may be provided between the nucleic acid extraction plate 1 and the plug 10 of the positive pressure device 7. One or more through holes are provided in the anti-contamination plate. The through hole matches with an inlet of the nucleic acid extraction column 1a on the nucleic acid extraction plate 1 and the plug 10 in pore diameter, so that the plug 10 is only in contact with an upper mouth of the through hole in the anti-contamination plate to avoid contamination caused by direct contact between the plug 10 and the inlet of the nucleic acid extraction column 1a. When the user adds a nucleic acid solution sample to be extracted to the nucleic acid extraction column 1a, contamination may occur at the inlet of the nucleic acid extraction column 1a.

The working principle of the present application is briefly described in the following.

Five to six kinds of chemical reagents for extracting or purifying nucleic acids are manually transferred into different reagent suppliers 8. The chemical reagent flows from the liquid outlet of the reagent supplier 8 to the liquid inlets of the reagent flow controller 9. The chemical reagent can be transported into the sealed chamber 5 of the infusion set 3 through the reagent flow controller 9. The liquid discharge volume or the start and stop of the liquid discharge operation of the needles 6 on the different sealed chambers 5 are controlled by the multiple reagent flow controllers 9. When the nucleic acid extraction plate 1 is moved to a position below the corresponding needle 6 for adding liquid to the nucleic acid extraction column 1a, the infusion set 3 is driven by the infusion set drive unit 3b to move downward to a position above the nucleic acid extraction column 1a to add liquid. After the liquid addition is finished, the infusion set 3 is driven again by the infusion set drive unit 3b to move upward, so that the needle 6 gets away from the nucleic acid extraction column 1a, and the subsequent positive pressure operation is performed. The nucleic acid extraction plate 1 is then moved to a position below the plug 10, and the positive pressure provider 12 is driven by the positive pressure drive device 7a to move downward, so that the plug 10 seals against the liquid inlet of the corresponding nucleic acid extraction column 1a. Then, the positive pressure provider 12 is started. The positive pressure device 7 can provide high-pressure gas, and the high-pressure gas acts on a surface of the solution (the solution includes the nucleic acid solution to be extracted or the chemical reagents). Since the high-pressure provided by the positive pressure device 7 directly acts on the solution surface of each nucleic acid extraction column 1a, the solution can quickly pass through the nucleic acid extraction column 1a and flow out. After the pressurization is completed, the positive pressure provider 12 is driven by the positive pressure drive device 7a to move upward to separate the plug 10 from the liquid inlet of the nucleic acid extraction column 1a.

In the process of pipetting, in a case that different chemical reagents need to be transferred in a same sealed chamber 5, a certain path through which the chemical reagents flow may be cleaned in advance. The specific method may include: filling a large amount of purified water into the reagent supplier 8 for many times, and high-pressure outputting the purified water through the needle 6, thereby realizing the cleaning of the path during the high-pressure output of the large amount of purified water.

Specifically, the nucleic acid extraction system further includes a stirring plate 14, a stirring plate mounting frame 14a and a stirring plate drive device 14b. The stirring plate mounting frame 14a is fixed on the installation frame 13, the stirring plate drive device 14b is arranged on the stirring plate mounting frame 14a, and the stirring plate 14 is arranged on the bottom of the stirring plate mounting frame 14a. Stirring rods 16 in one-to-one correspondence with the multiple nucleic acid extraction columns 1a are provided on the bottom of the stirring plate 14, and the stirring plate drive device 14b is configured to drive the stirring rods 16 to move up and down in the nucleic acid extraction columns 1a through the stirring plate mounting frame 14a. When the nucleic acid extraction plate 1 is moved to a position below the stirring plate 14, the stirring plate 14 is moved up and down, so that the solution in the nucleic acid extraction plate 1 can be well mixed.

Figure 4:
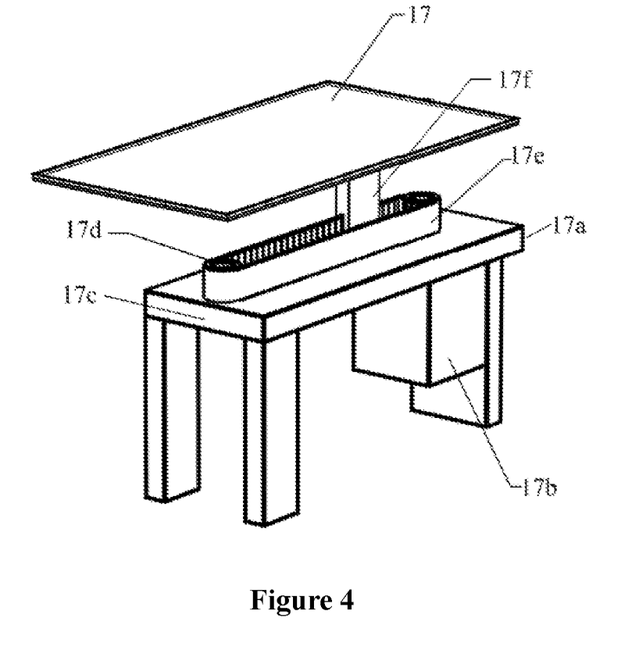
FIG. 4 is a schematic structural view of a first partition plate and a first partition plate drive device according to an embodiment of the present application.

Moreover, as shown in FIGS. 1 and 4, the nucleic acid extraction system further includes a first partition plate 17 and a first partition plate drive device 17a. The first partition plate 17 is arranged between the stirring rods 16 and the nucleic acid extraction plate 1. The first partition plate drive device 17a is fixed on the installation frame 13 and is configured to drive the first partition plate 17 to move horizontally below the stirring rods 16. After the solution in the nucleic acid extraction plate 1 is well mixed by the stirring plate 14, a little amount of solution may remain on the stirring rod 16. The first partition plate 17 is extended out by the first partition plate drive device 17a, so that the solution dripping from the stirring rod 16 falls on the first partition plate 17, and the solution remaining on the stirring rod 16 is prevented from dripping into other holes of the nucleic acid extraction plate 1 during the movement of the nucleic acid extraction plate 1, avoiding contamination during the nucleic acid extraction. When the stirring operation needs to be performed again, the first partition plate 17 is retracted by the first partition plate drive device 17a.

Figure 5:
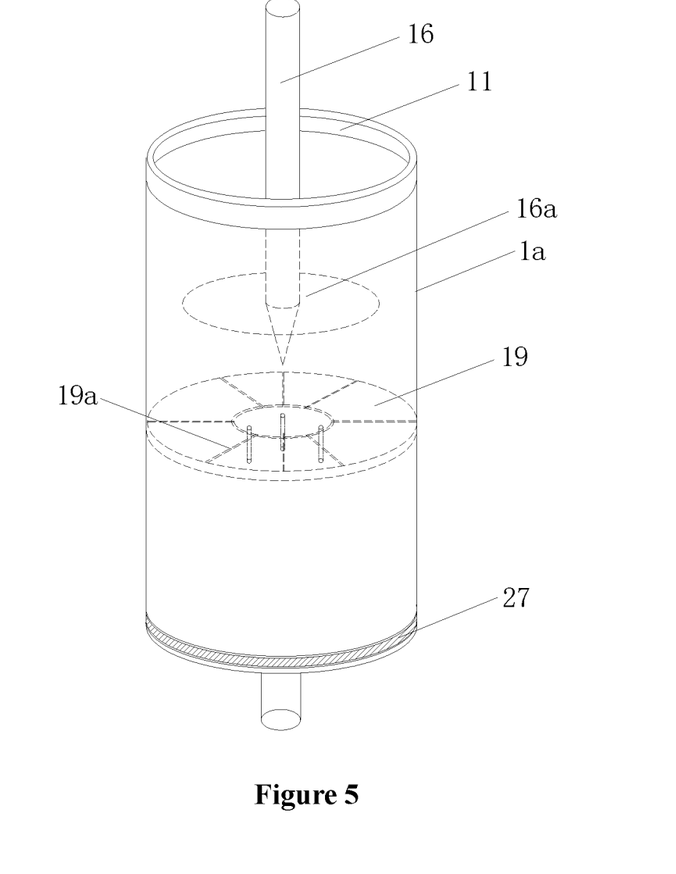
FIG. 5 is a schematic structural view showing that a stirring rod cooperates with an absorption column according to an embodiment of the present application.

Further, FIG. 5 is a schematic structural view showing that the stirring rod cooperates with an absorption column according to an embodiment of the present application. As shown in FIG. 5, the nucleic acid extraction column 1a includes an absorption column. The absorption column includes a breakable member 19 and an absorption membrane 27. The absorption membrane 27 covers the liquid outlet of the nucleic acid extraction column 1a. The breakable member 19 is arranged between the liquid inlet of the nucleic acid extraction column 1a and the absorption membrane 27, and is fixed on the inner wall of the nucleic acid extraction column 1a. The breakable member 19 is provided with a groove 19a, and the bottom of the stirring rod 16 is of a conical structure for piercing the groove 19a. The stirring rod 16 is sleeved with a stirring sheet 16a, and an outer diameter of the stirring sheet 16a is less than an inner diameter of the nucleic acid extraction column 1a. In the implementation, the stirring sheet 16a may be arranged at a lower portion of the stirring rod 16. The groove 19a may include an annular groove and multiple strip-shaped grooves, the annular groove is arranged at the center of the breakable member 19, the multiple strip-shaped grooves are arranged between the annular groove and an outer wall of the breakable member 19, and are arranged along a radius of the breakable member 19. When the plasmid DNA is extracted, the adsorption column can be used. Besides, the breakable member 19 is provided in the nucleic acid extraction column 1a, and before the breakable member 19 in the nucleic acid extraction column 1a is pierced, the nucleic acid extraction column 1a cooperates with the breakable member 19 as a test tube (no water outlet at the bottom) to hold the liquid, so that various chemical reagents react with each other here. After the breakable member 19 in the nucleic acid extraction column 1a is pierced, the liquid can flow out through the breakable member 19, so that the nucleic acid extraction column has the function of nucleic acid extraction and purification column, which can avoid using both the test tube and the nucleic acid extraction and purification column during nucleic acid extraction. Therefore, the pipetting speed is increased and the cost is reduced.

Figure 6:
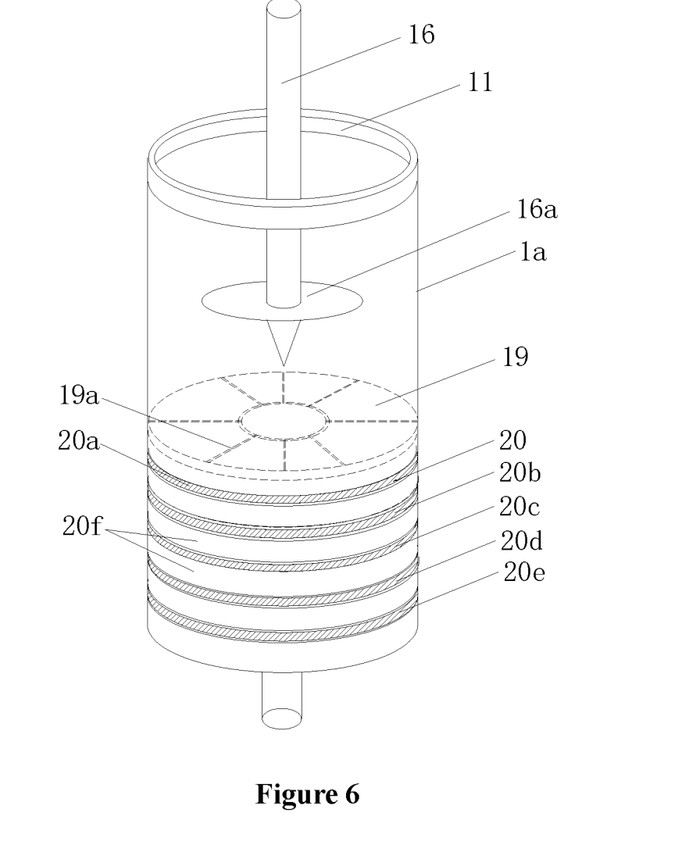
FIG. 6 is a schematic structural view showing that the stirring rod cooperates with a filter column according to an embodiment of the present application.

Further, FIG. 6 is a schematic structural view showing that the stirring rod cooperates with a filter column according to an embodiment of the present application. As shown in FIG. 6, the nucleic acid extraction column 1 includes a filter column. The filter column includes the breakable member 19 and multiple filter members 20. The breakable member 19 is arranged between the liquid inlet of the nucleic acid extraction column 1a and the liquid outlet of the nucleic acid extraction column 1a, and is fixed on the nucleic acid extraction column 1a. The breakable member 19 is provided with a groove 19a, and the bottom of the stirring rod 16 is of a conical structure for piercing the groove 19a. The stirring rod 16 is sleeved with a stirring sheet 16a, and an outer diameter of the stirring sheet 16a is less than the inner diameter of the nucleic acid extraction column 1a. The multiple filter members 20 are arranged between the breakable member 19 and the liquid outlet of the nucleic acid extraction column 1a, and are respectively fixed on an inner wall of the nucleic acid extraction column 1a. Each filter member 20 is provided with multiple filter micropores, and in two adjacent filter members 20, a pore diameter of the filter micropore of one filter member 20 close to the liquid inlet of the filter column is greater than the pore diameter of the filter micropore of another filter member 20 close to the liquid outlet of the filter column.

In the present embodiment, pore diameters of the multiple filter micropores of each filter member 20 are the same. In this way, it can be ensured that the solution flows evenly through the filter micropores, thus ensuring the filtering effect.

Further, the multiple filter members 20 may include at least three of a first filter member 20a, a second filter member 20b, a third filter member 20c, a fourth filter member 20d and a fifth filter member 20e. The first filter member 20a is provided with multiple first filter micropores, and the pore diameter of the multiple first filter micropores is 20 to 25 μm; the second filter member 20b is provided with multiple second filter micropores, and the pore diameter of the multiple second filter micropores is 16 to 19 μm; the third filter member 20c is provided with multiple third filter micropores, and the pore diameter of the multiple third filter micropores is 10 to 15 μm; the fourth filter member 20d is provided with multiple fourth filter micropores, and the pore diameter of the multiple fourth filter micropores is 5 to 9 μm; and the fifth filter member 20e is provided with multiple fifth filter micropores, and the pore diameter of the multiple fifth filter micropores is 1 to 4 μm. Multiple filter members 20 with different pore diameters are provided, and the pore diameter can be adjusted according to the size of solid-phase substances and plasmids in the solution to be filtered, so as to ensure that all solid-phase substances can be filtered out and the plasmids can flow out smoothly.

Further, the multiple filter members 20 include the first filter member 20a, the second filter member 20b, the third filter member 20c, the fourth filter member 20d and the fifth filter member 20e. The pore diameter of the multiple first filter micropores is 22 μm, the pore diameter of the multiple second filter micropores is 18 μm, the pore diameter of the multiple third filter micropores is 13 μm, the pore diameter of the multiple fourth filter micropores is 8 μm, and the pore diameter of the multiple fifth filter micropores is 2 μm. Such arrangement can ensure the filtering effect of the filter column.

Further, the filter column may further include a spacer ring 20f arranged between two adjacent filter members 20 and fixed on the inner wall of the filter column. The spacer ring 20f can keep the distance between two adjacent filter members 20, so as to avoid decrease of the filtering efficiency caused by two adjacent filter members 20 nestling against each other. In the present embodiment, the spacer ring 20f may be a polypropylene spacer ring, a polyethylene spacer ring or a polytetrafluoroethylene spacer ring.

The filter member 20 may be a filter screen plate, a filter membrane or a filter cotton, and the filter screen plate, the filter membrane and the filter cotton may be cooperatively used in a same filter column.

Referring to FIG. 3 again, a liquid level detection device 30 is provided on a side wall of the positive pressure provider 12. In the implementation, the liquid level detection device 30 may be a non-contact liquid level meter, for example, an ultrasonic sensor or an infrared sensor. The liquid level after being pressurized by the positive pressure device 7 can be monitored by the liquid level detection device 30. After the breakable member 19 is pierced, the liquid passes through the breakable member 19 and flows onto an upper surface of the filter member 20. At this time, if the nucleic acids to be extracted and purified are mixed with lump impurities (such as blood clots), the filter member 20 of the filter column may be blocked by the lump impurities, and the liquid thereby cannot pass through the filter member 20 smoothly, resulting in that a large amount of liquid is trapped at the upper surface of the filter member 20 and the nucleic acids to be extracted cannot be completely extracted and purified. During the specific operation, the nucleic acid extraction column 1a is moved to a position below the liquid level detection device 30, and the liquid level in the nucleic acid extraction column 1a is learned through the liquid level detection device 30, and whether the liquid completely passes through the filter member 20 is determined according to the liquid level. A siren (not shown)

may further be provided on the side wall of the positive pressure provider 12. The siren is electrically connected with the liquid level detection device 30. If the liquid does not completely pass through the filter member 20, an alarm signal may be issued by the siren.

Specifically, the nucleic acid extraction system further includes a first slide rail 21. The stirring plate 14, the pipetting device and the positive pressure device 7 are arranged side by side. The first slide rail 21 is arranged on the installation frame 13 along an arrangement direction of the stirring plate 14, the pipetting device and the positive pressure device 7. The first slide rail 21 is correspondingly arranged below the stirring rods 16, the infusion set 3 and the plugs 10, and the nucleic acid extraction plate 1 is slidably arranged on the first slide rail 21.

Figure 7:
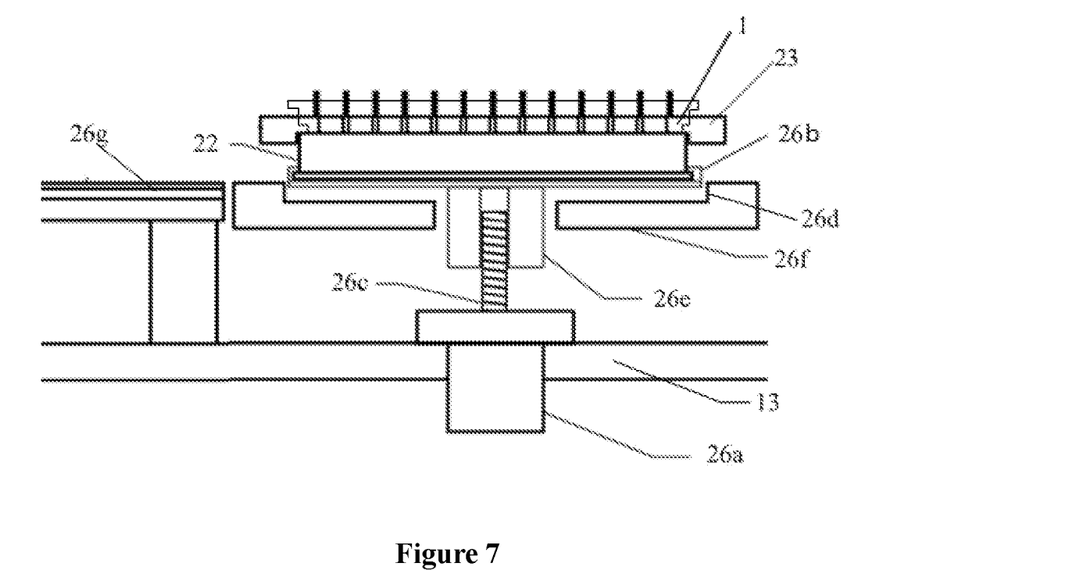
FIG. 7 is a schematic structural view of a lifting device according to an embodiment of the present application.

Further, FIG. 7 is a schematic structural view of a lifting device according to an embodiment of the present application. As shown in FIG. 7, the nucleic acid extraction system further includes a nucleic acid collection plate 22, a lifting device, a position-limiting snapping frame 23 and a position-limiting snapping frame drive device. The position-limiting snapping frame 23 is slidably arranged on the first slide rail 21. The lifting device 26 is arranged below the first slide rail 21. The lifting device includes a lifting motor 26a, a lifting device screw rod 26c, a lifting device screw nut 26e, a lifting position-limiting plate 26f, a lifting plate 26b and a second slide rail 26g (as shown in FIG. 1) for slidably supporting the nucleic acid collection plate 22. The lifting motor 26a is fixed on the installation frame 13, the lifting device screw rod 26c is in transmission connection with an output shaft of the lifting motor 26a, the lifting device screw nut 26e is sleeved on the lifting device screw rod 26c, the lifting position-limiting plate 26f is provided with a lifting snapping groove 26d, and the lifting plate 26b is snapped in the lifting snapping groove 26d and is movable along the lifting snapping groove 26d. The lifting device screw nut 26e passes through the lifting position-limiting plate 26f to be fixedly connected with a bottom surface of the lifting plate 26b, the nucleic acid collection plate 22 is arranged on a top surface of the lifting plate 26b, and the second slide rail 26g is flush with a top surface of the lifting position-limiting plate 26f and is in parallel with the first slide rail 21. The lifting plate 26b is lifted to the top surface of the lifting position-limiting plate 26f, until the height of the lifting plate 26b is the same as the height of the top surface of the lifting position-limiting plate 26f, so that the nucleic acid collection plate 22 can be moved from the lifting plate 26b to the second slide rail 26g and slide, following the position-limiting snapping frame 23, on the second slide rail 26g.

Figure 8:
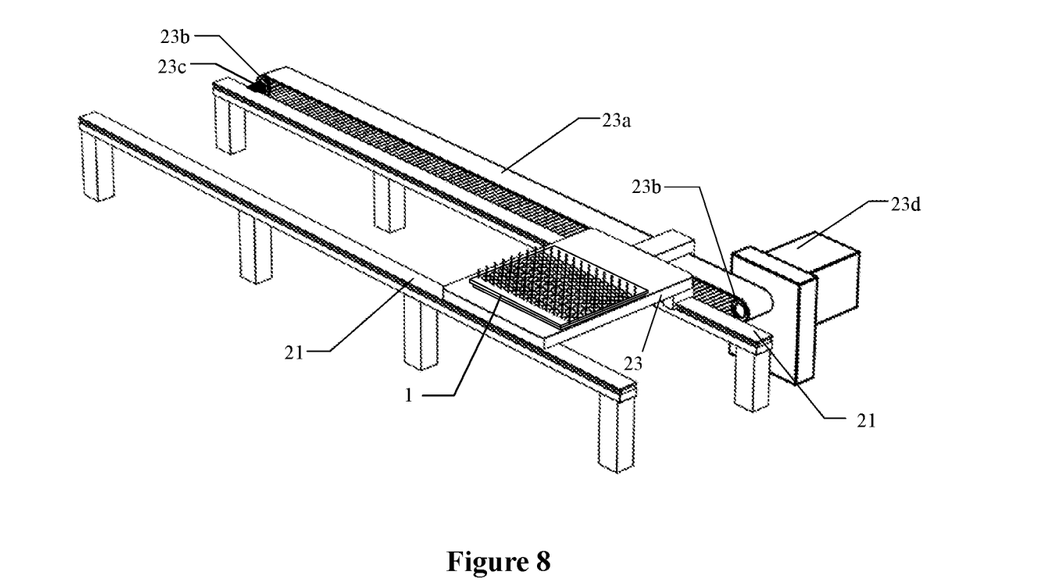
FIG. 8 is a schematic structural view of a position-limiting snapping frame and a position-limiting snapping frame drive device according to an embodiment of the present application.

FIG. 8 is a schematic structural view of the position-limiting snapping frame and the position-limiting snapping frame drive device according to an embodiment of the present application. As shown in FIG. 8, the position-limiting snapping frame drive device includes a belt 23a, belt pulleys 23b, a fixing rod 23c and a motor 23d fixed on the installation frame 13. The fixing rod 23c is fixed on a side wall of the first slide rail 21. Two belt pulleys 23b are provided and are respectively arranged on the output shaft of the motor 23d and the fixing rod 23c. The belt 23a is sleeved on the two belt pulleys 23b, and is in parallel with the first slide rail 21. The position-limiting snapping frame 23 is fixed on the belt 23a, a first snapping groove (not shown) for snapping the nucleic acid extraction plate 1 is provided on the top surface of the position-limiting snapping frame 23, and a second snapping groove (not shown) for snapping the nucleic acid collection plate 22 is provided on the bottom surface of the position-limiting snapping frame 23. The position-limiting snapping frame 23 may further provide the function of heating and shaking the nucleic acid extraction plate 1, so that the solution in the nucleic acid extraction column 1a is heated and shaken. Before the nucleic acids are eluted, the nucleic acid collection plate 22 is snapped on the bottom surface of the position-limiting snapping frame 23 through the upward movement of the lifting device 26, and the nucleic acid collection plate 22 is provided with nucleic acid collection tubes 22a (as shown in FIG. 1) which are in one-to-one correspondence with the nucleic acid extraction columns 1a. In the implementation, the 96-hole plate may be used as the nucleic acid collection plate 22. In order to lift the nucleic acid collection plate 22, the lifting motor 26a is activated, so that the lifting motor 26a drives the lifting device screw rod 26c to rotate, the lifting device screw nut 26e moves up and down along the lifting device screw rod 26c, and the lifting plate 26b moves, following the lifting device screw nut 26e, up and down in the lifting snapping groove 26d of the lifting position-limiting plate 26f. When the top surface of the lifting plate 26b is flush with the top surface of the lifting position-limiting plate 26f, the nucleic acid collection plate 22 can be snapped at the bottom of the position-limiting snapping frame 23, and the nucleic acid collection plate 22 can move together with the position-limiting snapping frame 23. At this time, the nucleic acid collection plate 22 moves from the lifting plate 26b to the second slide rail 26g by following the movement of the position-limiting snapping frame 23, and the nucleic acid collection plate 22 moves, following the position-limiting snapping frame 23, to a designated position.

In the implementation, two first slide rails 21 are provided two, and the two first slide rails 21 are arranged on two sides of the position-limiting snapping frame 23. Two second slide rails 26 are provided, the two second slide rails 26g are arranged on two sides of the nucleic acid collection plate 22, and the two second slide rails 26g are located between the two first slide rails 21.

Specifically, as shown in FIG. 1, the nucleic acid extraction system further includes a gripping frame 24 for gripping the nucleic acid extraction plate 1 and a gripping drive device 24a. A claw 24b corresponding to one edge of the nucleic acid extraction plate 1 is rotatably provided on the bottom of the gripping frame 24. A reset spring 24c for resetting the claw 24b is provided between the claw 24b and the gripping frame 24. The gripping drive device 24a is fixed on the installation frame 13 and is configured to drive the gripping frame 24 to move up and down. The gripping drive device 24a can lift or lower the gripping frame 24 as a whole. When the gripping frame 24 is lowered as a whole, after passing by the corresponding edge of the nucleic acid extraction plate 1 and being reset by the reset spring 24c, the claw 24b grips the nucleic acid extraction plate 1 at the bottom of the edge of the nucleic acid extraction plate 1, so as to avoid the user from taking the nucleic acid extraction plate 1 manually, which on the one hand reduces the workload of the user, and on the other hand, improves the degree of automation of the nucleic acid extraction system. In the implementation, the gripping frame 24 vertically arranged may be provided with a horizontal shaft and the claw 24b is arranged on the horizontal shaft. Moreover, in order to facilitate the rotation of the claw 24b, a bearing may be provided on the horizontal shaft, and the claw 24b is arranged on the bearing.

In the implementation, the nucleic acid extraction plate 1 is a 96-hole plate, and four claws 24b are provided. The four claws 24b respectively correspond to four sides of the nucleic acid extraction plate 1, so as to ensure the stability of gripping the nucleic acid extraction plate 1 and prevent the nucleic acid extraction plate 1 that has already been gripped from falling off.

Further, the nucleic acid extraction system further includes a second partition plate 25 and a second partition plate drive device 25a. The second partition plate 25 is arranged between the claw 24b and the nucleic acid extraction plate 1. The second partition plate drive device 25a is fixed on the installation frame 13 and is configured to drive the second partition plate 25 to move horizontally below the claw 24b. After the claw 24b grips the nucleic acid extraction plate 1, the solution remaining on the nucleic acid extraction plate 1 may drip off. The second partition plate 25 is extended out by the second partition plate drive device 25a, and the extended second partition plate 25 can intercept the solution dripped from the nucleic acid extraction plate 1.

In the present embodiment, as shown in FIG. 4, the structure of the second partition plate drive device 25a is the same as that of the first partition plate drive device 17a. Herein, the structure of the first partition plate drive device 17a is taken as an example to introduce the specific structure of the second partition plate drive device 25a. Specifically, the first partition plate drive device 17a includes a partition plate drive motor 17b, a partition plate drive mounting plate 17c, a partition plate rotating shaft 17d, a partition plate belt 17e and a partition plate mounting rod 17f. The partition plate drive mounting plate 17c is fixed on mounting frame 13, the partition plate drive motor 17b is fixed on the bottom of the partition plate drive mounting plate 17c, and both the output shaft of the partition plate drive motor 17b and the partition plate rotating shaft 17d pass through the partition plate drive mounting plate 17c. The partition plate belt 17e is arranged on the top surface of partition plate drive mounting plate 17c, and the partition plate belt 17e is sleeved on the output shaft of the partition plate drive motor 17b and the partition plate rotating shaft 17d for transmission. One end of the partition plate mounting rod 17f is arranged on the partition plate belt 17e, and the other end of the partition plate mounting rod 17f is arranged on the bottom of the first partition plate 17. In other embodiments, the second partition plate drive device 25a and the first partition plate drive device 17a may both adopt other driving modes.

Specifically, the reagent flow controller 9 may be a peristaltic pump, a diaphragm pump, a metering pump, a syringe pump, a plunger pump, a piston pump or a self-priming pump.

Figure 9:
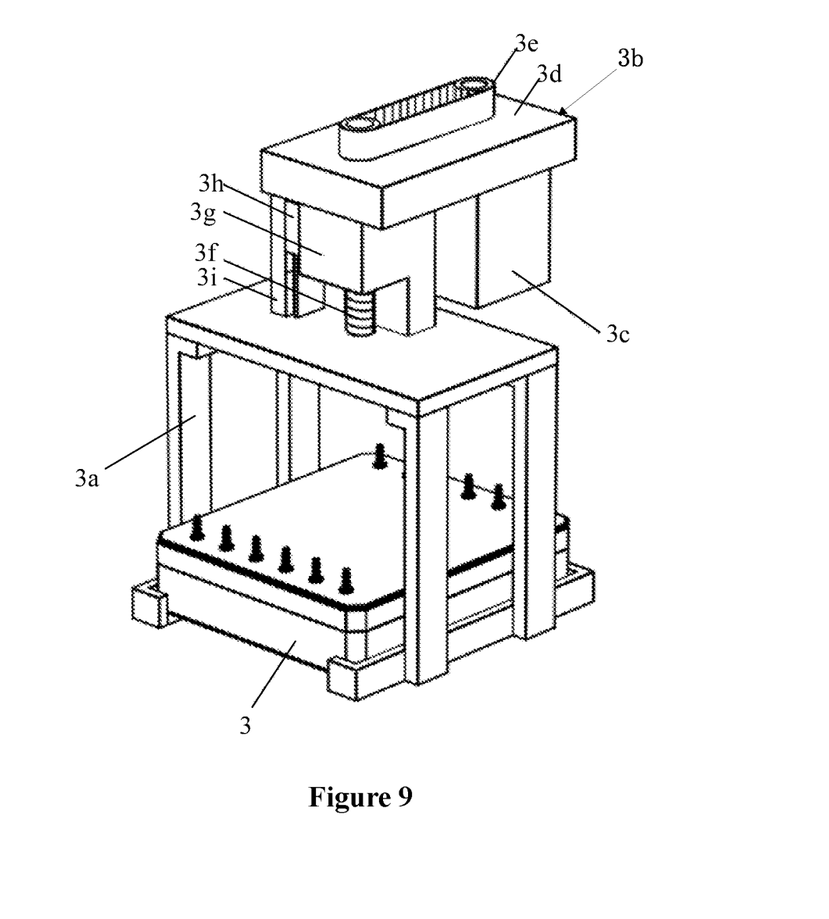
FIG. 9 is a schematic structural view of an infusion set drive unit according to an embodiment of the present application.
Figure 10:
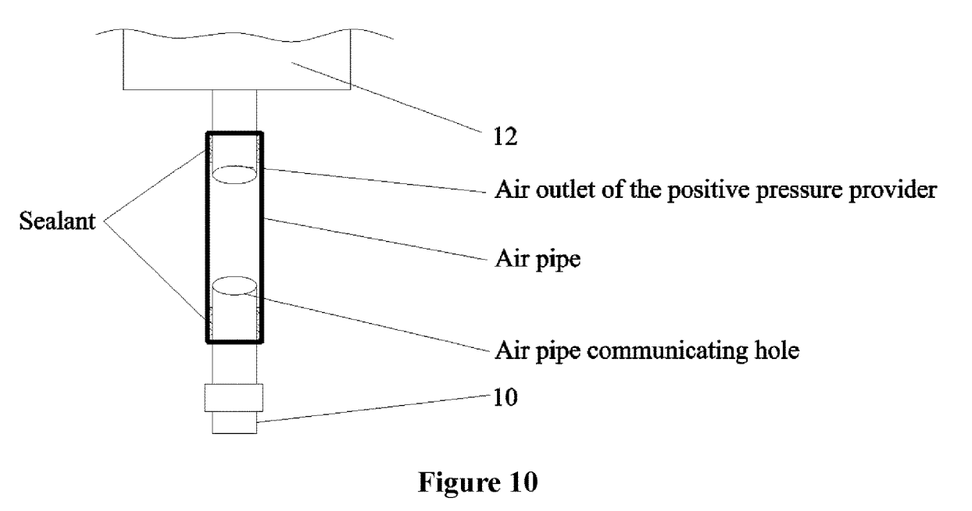
FIG. 10 is a schematic diagram showing the hermetic communication of an air pipe, a plug, and the positive pressure provider shown in FIG. 3.

The infusion set drive unit 3b, the positive pressure drive device 7a, the stirring plate drive device 14b and the gripping drive device 24a provided in the embodiment of the present application may be of the same driving structure, as shown in FIG. 9. The infusion set drive unit 3b is taken as an example for brief illustration. Specifically, the infusion set drive unit 3b includes an infusion set drive motor 3c, an infusion set drive mounting plate 3d, an infusion set belt 3e, a screw rod 3f, a screw rod nut block 3g, a screw rod nut slider 3h and a screw rod nut first slide rail 3i. The infusion set drive mounting plate 3d is fixed on the installation frame 13, the infusion set drive motor 3c is fixed on the bottom of the infusion set drive mounting plate 3d, and the output shaft of the infusion set drive motor 3c and the screw rod 3f pass through the infusion set drive mounting plate 3d. The infusion set belt 3e is arranged on the top surface of the infusion set drive mounting plate 3d, and the infusion set belt 3e is sleeved on the output shaft of the infusion set drive motor 3c and the screw rod 3f for transmission. The screw rod nut block 3g is screwed to the screw rod 3f, and the screw rod nut block 3g is fixed on the infusion set mounting frame 3a. The screw rod nut first slide rail 3i is arranged on the infusion set drive mounting plate 3d, the screw rod nut slider 3h is fixed on the screw rod nut block 3g, and the screw rod nut slider 3h is slidably arranged on the screw rod nut first slide rail 3i.

The working principle of the nucleic acid extraction system provided in the embodiment of the present application is briefly described in the following, which specifically is as follows:

First, six kinds of chemical reagents for extracting or purifying nucleic acids are manually transferred into different reagent suppliers 8.

1. If the nucleic acid such as plasmid DNA is to be extracted or purified, the plasmid DNA cell solution to be extracted or purified is manually filled into the nucleic acid extraction plate 1 on which the nucleic acid extraction column 1a is used as the filter column, and the nucleic acid extraction column 1a is provided with the breakable member 19 for preventing the solution from flowing further down. The liquid outlet of the nucleic acid extraction plate 1 on which the nucleic acid extraction column 1a is used as the filter column is aligned with the liquid inlet of the nucleic acid extraction plate 1 on which the nucleic acid extraction column 1a is used as the adsorption column. The two nucleic acid extraction plates 1 stacked together (the nucleic acid extraction column 1a of the upper nucleic acid extraction plate 1 is used as the filter column, and the nucleic acid extraction column 1a of the lower nucleic acid extraction plate 1 is used as the adsorption column) are placed on the position-limiting snapping frame 23 (a starting position) and snapped in the position-limiting snapping frame 23. At this time, the two nucleic acid extraction plates stacked together can move together with the position-limiting snapping frame 23. In addition, the nucleic acid collection plate 22 needs to be manually placed on the lifting plate 26b, and the subsequent process is automatically completed by the system without manual operation.

The position-limiting snapping frame 23 is moved to a position below the pipetting device, each row of filter columns on the nucleic acid extraction plate 1 successively receive a first chemical reagent outputted from a first row of needles 6 below the pipetting device at first and then are moved to a position below the stirring plate 14, and then the stirring rods 16 are extended into the corresponding filter columns and moved up and down, so that the solution in the filter columns is well mixed, and then the stirring rods 16 are moved up and away from the liquid inlets of the filter columns. The first partition plate 17 is extended to a position between the stirring rods 16 and the liquid inlets of the filter columns, and the liquid that may drip from the stirring rods 16 is intercepted by the first partition plate 17, thus preventing contamination.

Then, the position-limiting snapping frame 23 is moved to a position below the pipetting device, each filter column in each row successively receives a second chemical reagent outputted from a second row of needles 6 below the pipetting device at first and then is moved to a position below the stirring plate 14, and then the stirring rods 16 are extended into the corresponding filter columns and moved up and down, so that the solution in the filter columns is well mixed. At this time, the plasmid DNA cell solution to be extracted or purified in the filter columns reacts with the two chemical reagents, the cells are ruptured, the plasmid DNA dissolves in the liquid, and the genomic DNA and protein undergo a denaturation reaction and merge into flocculent solid-phase impurities. Then, the stirring rod 16 is moved further downward by a little distance in the filter column, so that the lower end of the stirring rod 16 pierces the breakable member 19 in the filter column, and the liquid in the filter column can flow downward through a crevasse in the breakable member 19 and flow onto the filter member 20.

Then, the position-limiting snapping frame 23 is moved to a position below the positive pressure device 7 to be pressurized. The solution containing the plasmid DNA in the filter column successively passes through the crevasse, the multiple filter members 20 and the liquid outlet of the filter column and flows into the lower adsorption column, while the solid-phase impurities pass through the crevasse and are filtered out by the multiple filter members 20 in the filter column.

Then, the position-limiting snapping frame 23 is moved to a position below the gripping frame 24, the upper nucleic acid extraction plate 1 (on which the nucleic acid extraction column 1a is used as the filter column) is lifted after being gripped by the gripping frame 24, so that the upper nucleic acid extraction plate is separated from the lower nucleic acid extraction plate 1 (on which the nucleic acid extraction column 1a is used as the adsorption column). Then, the second partition plate 25 is extended to a position below the upper nucleic acid extraction plate 1, and the liquid that may drip from the liquid outlet of the filter column 1a is intercepted by the second partition plate 25, thus preventing contamination.

Then, the position-limiting snapping frame 23 (at this time, only one nucleic acid extraction plate 1, on which the nucleic acid extraction column 1a is used as the adsorption column, is still on the position-limiting snapping frame 23) is moved to a position below the positive pressure device to successively pressurize the nucleic acid extraction columns 1a, the solution in the adsorption column flows out to a waste liquid basin 15 below the nucleic acid extraction plate 1 on which the nucleic acid extraction column 1a is used as the adsorption column, and the plasmid DNA in the solution is adsorbed by an adsorption membrane 27 in the adsorption column.

Then, the position-limiting snapping frame 23 is moved to a position below the pipetting device, the nucleic acid extraction columns 1a successively receive a third chemical reagent (a first rinse liquid) outputted from a third row of needles 6 at first and then are moved to a position below the positive pressure device 7 for pressurization, the plasmid DNA on the membrane is rinsed by the first rinse liquid when the first rinse liquid passes through the adsorption membrane, and then the first rinse liquid flows out to the waste liquid basin 15 below the nucleic acid extraction plate 1. In the implementation, the waste liquid basin 15 is arranged on the installation frame 13 between the two second slide rails 26g. The waste liquid basin 15 may be embedded in the installation frame 13, the bottom of the waste liquid basin 15 may be connected with a waste liquid bottle through a hose, and the waste liquid collected in the waste liquid basin 15 can flow into the waste liquid bottle through the hose. After the waste liquid bottle is full of the waste liquid, the waste liquid can be poured out and the waste liquid bottle can be reused.

Then, the position-limiting snapping frame 23 is moved to a position below the pipetting device, and the nucleic acid extraction columns 1a successively receive a fourth chemical reagent (a second rinse liquid) and a fifth chemical reagent (a third rinse liquid) outputted from a fourth row and a fifth row of needles 6 at first, and the following process is similar to that with the first rinse liquid.

Then, the position-limiting snapping frame 23 is moved to the starting position, the lifting device screw rod 26c is driven to rotate by the lifting motor 26a, so that the lifting device screw nut 26e drives the lifting plate 26b to rise, and at this time, the nucleic acid collection plate 22 located on the lifting plate 26b is snapped at the bottom of the position-limiting snapping frame 23, so that the nucleic acid collection plate 22 can move, following the position-limiting snapping frame 23, on the first slide rail 26g of the lifting device. At this time, the liquid inlet of the nucleic acid collection tube 22a on the nucleic acid collection plate 22 below the position-limiting snapping frame 23 corresponds to the liquid outlet of the nucleic acid extraction column 1a above the position-limiting snapping frame 23. Then, the position-limiting snapping frame 23 is moved to a position below the pipetting device, the adsorption columns of the nucleic acid extraction plate 1 successively receive a sixth chemical reagent (an eluent) outputted from a sixth row of needles and then are moved to a position below the positive pressure device 7 for pressurization. The plasmid DNA departs, following the eluent, from the absorption membrane of the absorption column and flows into the nucleic acid collection plate 22. Then, the position-limiting snapping frame 23 with the nucleic acid extraction plate 1 and the nucleic acid collection plate 22 is moved to the starting position to complete the extraction or purification of the plasmid DNA.

2. If the nucleic acid to be extracted or purified is genomic DNA, viral DNA or RNA, no filter plate is needed, and the process is relatively simple. Firstly, the nucleic acid extraction plate 1 on which the nucleic acid extraction column 1a is used as the adsorption column is manually filled with the nucleic acid cell solution to be extracted or purified, and the adsorption column is provided with the breakable member 19 for preventing the liquid from flowing further down. The nucleic acid extraction plate 1 on which the nucleic acid extraction column 1a is used as the adsorption column is snapped in the position-limiting snapping frame 23, so that the nucleic acid extraction plate 1 on which the nucleic acid extraction column 1a is used as the adsorption column can move together with the position-limiting snapping frame 23. In addition, the nucleic acid collection plate 22 needs to be manually placed on the lifting plate 26b, and the subsequent process is automatically completed by the system without manual operation.

The position-limiting snapping frame 23 is moved to a position below the pipetting device, the adsorption columns of the nucleic acid extraction plate 1 successively receive the first chemical reagent outputted from the first row of needles 6 and then are moved to a position below the stirring plate 14, so that the solution is mixed well by the stirring rods 16. The stirring plate 14 is moved up so that the stirring rods 16 get away from the liquid inlets of the absorption columns, then the first partition plate 17 is extended to a position between the stirring rods 16 and the liquid inlets of the absorption columns. Then, the position-limiting snapping frame 23 is moved to a position below the pipetting device, the adsorption columns of the nucleic acid extraction plate 1 successively receive the second chemical reagent outputted from the second row of needles 6. Then, the position-limiting snapping frame 23 is moved to a position below the stirring plate 14, and the solution therein is then well mixed. At this time, the cells are ruptured, and the nucleic acids are released into the solution. Then, the stirring rod 16 is moved further downward by a little distance in the filter column, so that the breakable member 19 is pierced by the stirring rod 16. Then, the position-limiting snapping frame 23 is moved to a position below the positive pressure device 7, so that the absorption columns on the nucleic acid extraction plate 1 are pressurized. The fluid flows out through the absorption membrane 27 and is received by the waste liquid basin 15, and the nucleic acids are adsorbed by the adsorption membrane 27. Then the position-limiting snapping frame 23 is moved to a position below the pipetting device, and the adsorption columns of the nucleic acid extraction plate 1 successively receive the third to fifth chemical reagents (rinse liquid) outputted from the third to fifth rows of needles 6. Each time after adding the rinse liquid, the position-limiting snapping frame is moved to a position below the positive pressure device 7. The nucleic acids in the absorption membrane 27 are rinsed by the rinse liquid, and then the rinse liquid flows out to the waste liquid basin 15. Then the position-limiting snapping frame 23 is moved to the starting position. The lifting device screw rod 26c is driven to rotate by the lifting motor 26a, so that the lifting device screw nut 26e drives the lifting plate 26b to rise, and at this time, the nucleic acid collection plate 22 located on the lifting plate 26b is snapped at the bottom of the position-limiting snapping frame 23, so that the nucleic acid collection plate 22 can move, following the position-limiting snapping frame 23, on the first slide rail 26g of the lifting device. Then the position-limiting snapping frame 23 is moved to a position below the pipetting device, the absorption columns on the nucleic acid extraction plate 1 successively receive the sixth chemical reagent (an eluent). Then the position-limiting snapping frame 23 is moved to a position below the positive pressure device 7 for pressurization. The DNA on the absorption membrane 27 is eluted into the nucleic acid collection plate 22. Then, the position-limiting snapping frame 23 is moved to the starting position to complete the extraction or purification of the nucleic acids.

According to the nucleic acid extraction system provided by the embodiment of the present application, When a certain chemical reagent is required for nucleic acid extraction or purification, the chemical reagent can be transported from the reagent supplier into the sealed chamber of the infusion set at fixed time and by fixed quantity through the reagent flow controller, and can be high-pressure outputted through needles, which enables the nucleic acid extraction system provided by the embodiment to dispense with the automatic pipetting workstation and high-quality pipette tips, thus improving the pipetting speed and reducing the cost. Besides, since the plug hermetically communicates with the nucleic acid extraction column, a high-pressure gas can be introduced into the nucleic acid extraction column by the positive pressure provider, and the liquid in the nucleic acid extraction column can overcome the resistance of the membrane inside the column and quickly flow out, which avoids the troublesome operation and waste of time brought by using the centrifuge or negative pressure machine, and further improves the nucleic acid extraction efficiency and reduces the cost of extraction.

In the above embodiment, the positions of various components in the nucleic acid extraction system are not necessarily as shown in the figures, but can be interchanged. For example, the positions of infusion set, positive pressure device and stirring device in the system can be interchanged or one component can be placed above or below another component.

The foregoing shows only preferred embodiments of the present application and is not intended to limit the present application, and any modifications, equivalent substitutions and improvements within the spirit and the principle of the present application are included within the protection scope of the present application.

The invention claimed is:

1. A nucleic acid extraction system, comprising an installation frame, a nucleic acid extraction plate, a pipetting device and a positive pressure device, wherein the pipetting device and the positive pressure device are arranged side by side,
    the pipetting device comprises an infusion set, an infusion set mounting frame, an infusion set drive unit and a plurality of infusion units, the infusion set comprises sealed chambers which correspond to the plurality of infusion units in one-to-one correspondence, the sealed chambers are arranged side by side, a needle is provided on the bottom of each sealed chamber, each needle is in communication with the corresponding sealed chamber, the infusion set is arranged on the bottom of the infusion set mounting frame, and the infusion set drive unit is fixed on the installation frame and is configured to drive the infusion set to move up and down through the infusion set mounting frame;
    each infusion unit comprises a reagent supplier and a reagent flow controller, and in each infusion unit, a liquid outlet of the reagent supplier is in communication with a liquid inlet of the reagent flow controller, and a liquid outlet of the reagent flow controller is in communication with the corresponding sealed chamber;
    the positive pressure device comprises a plurality of plugs, a plurality of corresponding air pipes, a positive pressure provider and a positive pressure drive device, each of the plugs is provided with an air pipe communicating hole, one end of a corresponding air pipe hermetically communicates with the air pipe communicating hole and another end of the corresponding air pipe hermetically communicates with an air outlet of the positive pressure provider, and the positive pressure drive device is fixed on the installation frame and is configured to drive the positive pressure provider to move up and down; and
    a plurality of nucleic acid extraction columns are provided on the nucleic acid extraction plate, the plurality of nucleic acid extraction columns are correspondingly arranged below the needles or the plugs, a liquid inlet of each nucleic acid extraction column is provided with a sealing gasket which is in a sealing fit with the corresponding plug, and the nucleic acid extraction column is detachably and hermetically connected with the corresponding plug.

2. The nucleic acid extraction system according to claim 1, further comprising a stirring plate, a stirring plate mounting frame and a stirring plate drive device, wherein the stirring plate mounting frame is fixed on the installation frame, the stirring plate drive device is arranged on the stirring plate mounting frame, the stirring plate is arranged on the bottom of the stirring plate mounting frame, stirring rods in a one-to-one correspondence with the plurality of nucleic acid extraction columns are provided on the bottom of the stirring plate, and the stirring plate drive device is configured to drive the stirring rods to move up and down in the nucleic acid extraction columns through the stirring plate mounting frame.

3. The nucleic acid extraction system according to claim 2, further comprising a first partition plate and a first partition plate drive device, wherein the first partition plate is arranged between the stirring rods and the nucleic acid extraction plate, and the first partition plate drive device is fixed on the installation frame and is configured to drive the first partition plate to move horizontally below the stirring rods.

4. The nucleic acid extraction system according to claim 2, wherein each of the nucleic acid extraction columns comprises a filter column which comprises a breakable member and a plurality of filter members, the breakable member is arranged between the liquid inlet of the nucleic acid extraction column and a liquid outlet of the nucleic acid extraction column, and is fixed on the nucleic acid extraction column, the breakable member is provided with a groove, and the bottom of the corresponding stirring rod is of a conical structure for piercing the groove;

the stirring rod is sleeved with a stirring sheet, and an outer diameter of the stirring sheet is less than an inner diameter of the nucleic acid extraction column;

the plurality of filter members are arranged between the breakable member and the liquid outlet of the nucleic acid extraction column, and are fixed on an inner wall of the nucleic acid extraction column, each filter member is provided with a plurality of filter micropores, and in two adjacent filter members, a pore diameter of the filter micropores of one filter member closer to the liquid inlet of the filter column is greater than the pore diameter of the filter micropores of the other filter member closer to the liquid outlet of the filter column.

5. The nucleic acid extraction system according to claim 2, wherein each of the nucleic acid extraction columns comprises an absorption column which comprises a breakable member and an absorption membrane, the absorption membrane covers a liquid outlet of the nucleic acid extraction column, and the breakable member is arranged between the liquid inlet of the nucleic acid extraction column and the absorption membrane and is fixed on an inner wall of the nucleic acid extraction column; and the breakable member is provided with a groove, and the bottom of the corresponding stirring rod is of a conical structure for piercing the groove, the stirring rod is sleeved with a stirring sheet, and an outer diameter of the stirring sheet is less than an inner diameter of the nucleic acid extraction column.

6. The nucleic acid extraction system according to claim 2, further comprising a first slide rail, wherein the stirring plate, the positive pressure device and the pipetting device are arranged side by side, the first slide rail is arranged on the installation frame along an arrangement direction of the stirring plate, the pipetting device and the positive pressure device, the first slide rail is below the stirring rods, the infusion set and the plugs, and the nucleic acid extraction plate is slidably arranged on the first slide rail.

7. The nucleic acid extraction system according to claim 6, further comprising a nucleic acid collection plate, a lifting device, a position-limiting snapping frame and a position-limiting snapping frame drive device, wherein the position-limiting snapping frame is slidably arranged on the first slide rail, and the lifting device is arranged below the first slide rail;

the lifting device comprises a lifting motor, a lifting device screw rod, a lifting device screw nut, a lifting position-limiting plate, a lifting plate and a second slide rail for slidably supporting the nucleic acid collection plate, wherein the lifting motor is fixed on the installation frame, the lifting device screw rod is in transmission connection with an output shaft of the lifting motor, the lifting device screw nut is sleeved on the lifting device screw rod, the lifting position-limiting plate is provided with a lifting snapping groove, the lifting plate is snapped in the lifting snapping groove, the lifting device screw nut passes through the lifting position-limiting plate to be fixedly connected with a bottom surface of the lifting plate, the nucleic acid collection plate is arranged on a top surface of the lifting plate, and the second slide rail is flush with a top surface of the lifting position-limiting plate and is in parallel with the first slide rail; and the position-limiting snapping frame drive device comprises a belt, belt pulleys, a fixing rod and a motor fixed on the installation frame, wherein the fixing rod is fixed on a side wall of the first slide rail, two belt pulleys are provided and are respectively installed on an output shaft of the motor and the fixing rod, the belt is sleeved on the two belt pulleys and is in parallel with the first slide rail, the position-limiting snapping frame is fixed on the belt, a first snapping groove for snapping the nucleic acid extraction plate is provided on a top surface of the position-limiting snapping frame, the nucleic acid extraction plate is arranged in the first snapping groove, a second snapping groove for snapping the nucleic acid collection plate is provided on a bottom surface of the position-limiting snapping frame, and the nucleic acid collection plate is provided with nucleic acid collection tubes which are in one-to-one correspondence with the nucleic acid extraction columns.

8. The nucleic acid extraction system according to claim 1, further comprising a gripping frame for gripping the nucleic acid extraction plate and a gripping drive device, wherein a claw for clamping one edge of the nucleic acid extraction plate is rotatably provided on the bottom of the gripping frame, a reset spring for resetting the claw is provided between the claw and the gripping frame, and the gripping drive device is fixed on the installation frame and is configured to drive the gripping frame to move up and down.

9. The nucleic acid extraction system according to claim 8, further comprising a residual-solution receiving plate and a residual-solution receiving plate drive device, wherein the residual-solution receiving plate is arranged below the claw, and the residual-solution receiving plate drive device is fixed on the installation frame and is configured to drive the residual-solution receiving plate to move horizontally below the claw.

10. The nucleic acid extraction system according to claim 1, wherein a liquid level detection device is provided on a side wall of the positive pressure provider.

11. The nucleic acid extraction system according to claim 1, further comprising a pressure sensor and a pressure alarm, wherein the pressure sensor is arranged on an outer wall of the air pipe and configured to detect pressure in the air pipe, and when the pressure detected by the pressure sensor exceeds a preset pressure range, the pressure alarm issues an alarm.

* * * * *